United States Patent [19]

Matsuda et al.

[11] 4,376,205

[45] Mar. 8, 1983

[54] PROCESS FOR THE PREPARATION OF INDOLES FROM ANILINES AND ETHANOLAMINES

[75] Inventors: Fujio Matsuda, Kanagawa; Takazo Kato, Ohimachi, both of Japan

[73] Assignee: Mitsui Toatsu Chemicals, Inc., Tokyo, Japan

[21] Appl. No.: 254,549

[22] Filed: Apr. 15, 1981

[51] Int. Cl.³ .......................................... C07D 209/02
[52] U.S. Cl. ................................................. 548/508
[58] Field of Search ..................... 260/319.1; 548/508

[56] References Cited

U.S. PATENT DOCUMENTS 3,699,120  10/1972  Bakke et al. .................. 260/319.1
3,984,434  10/1976  O'Murchu ..................... 260/319.1

FOREIGN PATENT DOCUMENTS 50-197608  3/1975  Japan ................................ 548/508
55-105663  2/1979  Japan ............................ 260/319.1
55-108850  8/1980  Japan ................................ 548/508
56-36451   of 1981 Japan ................................ 548/508

OTHER PUBLICATIONS

J.A.C.S., Heine et al., "The Synthesis of Some N-Arylethylenimines", 76, 2503 (1954), p. 2503.
Ind. Eng. Chem., Prod. Res. Dev., vol. 15, No. 3, 1976, Bhattacharyya and Nandi, "Synthesis of N-N-Dimethylaniline from Aniline and Methanol", pp. 201–206.
Chemical Abstracts, 66, 75974s, (1967), pp. 7126–7127.
Chemical Abstracts, 70, 78437n, (1969), p. 6.
Ind. Eng. Chem. 43(7), 1579, (1951), Catalytic Reactions of Aromatic Amines, Alkylation with Alcohols, Hill et al.
Chemical Abstracts, 82, P170329z, (1975), Governale et al.
J.A.C.S., 101:2, Jan. 17, 1979, Reactions of Aniline with Olefins Catalyzed by Group 8 Metal Complexes: N-Alkylation and Heterocycle Formation.
"Classification of Catalysts by Reactions", edited by Tarama Laboratory Staff of Kyoto University, Japan, published by Kagaku Kogyo Sha (Chemical Industrial Co.) of Tokyo, Japan, pp. 74–76, (Sep. 1, 1971). (With Translation).
Tanabe, "Solid Acids and Bases", Acad. Press, NY, pp. 1–3, (1970).
"Classification of Catalysts by Reactions," Kagaku Kogyo Sha, (Chemical Industrial Co.), pp. 74–76, (Sep. 1, 1971).

Primary Examiner—Donald G. Daus
Assistant Examiner—D. B. Springer
Attorney, Agent, or Firm—Fisher, Christen & Sabol

[57] ABSTRACT

A process for the preparation of indole and derivatives thereof wherein an aniline is reacted with an ethanolamine in the vapor phase, the liquid phase or a mixed vapor-liquid phase. Various solid acids, metals and activated carbon can be used as catalysts for this reaction. The present invention makes it possible to prepare indole and derivatives thereof in a single step by using inexpensive compounds as the starting materials.

11 Claims, No Drawings

PROCESS FOR THE PREPARATION OF INDOLES FROM ANILINES AND ETHANOLAMINES

BACKGROUND OF THE INVENTION (1) Field of the Invention

This invention relates to a novel process for the preparation of indole and derivatives thereof by reacting an aniline with an ethanolamine.

(2) Description of the Prior Art

In the prior art, indole derivatives have long been prepared by the well-known Fischer indole synthesis in which phenylhydrazine is reacted with a compound having an aldehyde group. If the aldehyde compound is other than acetaldehyde, the aforesaid Fischer indole synthesis can be applied to obtain indole derivatives in good yield. However, if the aldehyde compound is acetaldehyde, no reaction that yields indole has been believed to take place. In order to overcome this disadvantage, there has recently been proposed an improved process which comprises reacting phenylhydrazine with acetaldehyde at an elevated temperature of from 300° to 400° C. in the presence of an alumina catalyst (Japanese Patent Laid-Open No. 76864/'73).

This process surely permits the reaction to proceed and brings about the formation of indole, but fails to give a satisfactory yield. Moreover, it is greatly disadvantageous in that the catalyst has so short a life as to become totally inactive after 0.5–1 hour's use.

Indole can also be prepared by another process which comprises reacting o-toluidine with formic acid to form o-methyl-N-formylaniline and then fusing it together with potassium hydroxide. However, it is usually impossible to selectively prepare o-toluidine that is used as the starting material in this process. That is, the p-isomer is always formed in an amount equal to or greater than that of the o-isomer. Thus, treatment of the isomer formed as a by-product poses a serious problem in the case of industrial production. Moreover, the handling of solids as in alkali fusion is troublesome. For these reasons, the aforesaid process cannot be regarded as suitable for industrial purposes.

Furthermore, a number of attempts have been made to synthesize indole from N-β-hydroxyethylamine, but none of them are satisfactory from an industrial point of view. For example, a process which comprises effecting the reaction at 300° C. in the presence of an aluminosilicate catalyst [Zhur. Obschue. Khin., Vol. 24, pp. 671–678 (1954)] gives only a very low yield of indole. A process which comprises heating the reactant together with a molten mixed salt consisting mainly of zinc chloride (Japanese Patent Laid-Open No. 57968/'73) can give a fairly high yield of indole. However, this process has the disadvantage of requiring a complicated procedure, which makes it unsuitable for industrial purposes.

As described above, a number of processes for the synthesis of indole and derivatives thereof have been proposed. However, many of them are disadvantageous in that large amounts of by-products are formed, expensive compounds are used as the starting materials, and/or lengthy and complicated procedures are required to obtain the desired products.

SUMMARY OF THE INVENTION

It is an object of the present invention to provide a one-step process for the highly selective preparation of indole and derivatives thereof by using inexpensive compounds as the starting materials.

According to the present invention, there is provided a process for the preparation of indole and derivatives thereof which comprises reacting an aniline with an ethanolamine.

This reaction can be carried out both in the liquid phase and in the vapor phase. By way of example, the process of the present invention makes it possible to obtain indole by reacting aniline with an ethanolamine and to obtain 5-methylindole by reacting p-toluidine with an ethanolamine.

Thus, the process of the present invention has a number of advantages. First, the anilines and ethanolamines which can be used as the starting materials are very inexpensive. Secondly, the preparation of indole or a derivative thereof from the starting materials can be achieved in a single step. Thirdly, by-products are scarcely formed and a very high selectivity is attained, so that indole or a derivative thereof can be obtained in highly pure form.

DETAILED DESCRIPTION OF THE INVENTION

The aniline used in the process of the present invention is a compound of the general formula

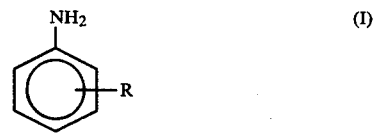

where R represents a hydrogen atom, halogen atom, hydroxyl group, alkyl group or alkoxy group. Specific examples thereof are aniline, o-toluidine, m-toluidine, p-toluidine, o-haloanilines, p-haloanilines, m-haloanilines, o-aminophenol, m-aminophenol, p-aminophenol, o-anisidine, m-anisidine, and p-anisidine.

The ethanolamine used in the process of the present invention is a member selected from the group consisting of monoethanolamine, diethanolamine, and triethanolamine.

Although the process of the present invention can be carried out in the absence of catalyst, it is preferably carried out in the presence of a solid acid catalyst, a metallic catalyst or activated carbon to obtain the desired product in good yield.

The solid acid catalysts which can be used in the process of the present invention fall under the following three categories:

(1) Catalysts containing an oxide or hydroxide (hereinafter referred to as the catalytic substance (1)) of at least one element selected from the group consisting of Si, Al, B, Sb, Bi, Sn, Pb, Ga, Ti, Zr, Be, Mg, Y, Ag, Zn, Cd and the lanthanides. Specific examples of the catalytic substance (1) are CdO, ZnO-Sb$_2$O, PbO$_2$, Al$_2$O$_3$-B$_2$O$_3$, SiO$_2$-CdO, SiO$_2$-Al$_2$O$_3$, SiO$_2$-MgO, TiO$_2$-SnO$_2$, TiO$_2$-ZrO$_2$, CdO-Bi$_2$O$_3$, SiO$_2$-Y$_2$O$_3$, SiO$_2$, Bi$_2$O$_3$-BeO, SiO$_2$-Ga$_2$O$_3$, SiO$_2$-La$_2$O$_3$, SiO$_2$-Ce$_2$O$_3$, SiO$_2$-ZnO-AgO, SiO$_2$-MgO-CuO and the like.

(2) Catalysts containing a sulfide or selenide (hereinafter referred to as the catalytic substance (2)) of at least one element selected from the group consisting of Pd, Pt, Cr, Fe, Ni, Co, Zn, Mo, Cd and W. Specific examples of the catalytic substance (2) are PdS, PtS, CrS, FeS, NiS, CoS, ZnS, MoS$_2$, CdS, WS$_2$, ZnSe, CdSe and the like.

(3) Catalysts containing an inorganic acid salt (hereinafter referred to as the catalytic substance (3)) of at least one element selected from the group consisting of Fe, Tl, Ca, Mn, Bi, Sr, Y, Al, Zn, Cd, Ni, Mg, In, Be, Co, Ga and the lanthanides. The useful inorganic acid salts include halides, carbonates, nitrates, sulfates, phosphates, pyrophosphates, phosphomolybdates and silicotungstates, and specific examples of the catalytic substance (3) are ferric sulfate, thallium sulfate, calcium sulfate, manganese sulfate, bismuth sulfate, strontium sulfate, yttrium sulfate, cadmium bromide, aluminum sulfate, zinc sulfate, nickel sulfate, cadmium chloride, magnesium sulfate, indium sulfate, beryllium sulfate, cadmium nitrate, cobalt sulfate, zinc aluminum sulfate, magnesium chloride, cadmium sulfate, cadmium phosphate and the like.

The metallic catalysts which can be used in the process of the present invention include catalysts containing at least one element (hereinafter referred to as the catalytic substance (4)) selected from the group consisting of Cu, Ag, Pt, Pd, Ni, Co, Fe, Ir, Os, Ru and Rh.

The solid acid catalysts and metallic catalysts which are usable in the process of the present invention can be prepared by any suitable methods that are known in this field of art. More specifically, solid acid catalysts falling under the category of the catalytic substance (1) can be prepared, for example, by hydrolyzing a water-soluble salt of the principal constituent element of the desired catalyst to form its hydroxide and then drying and calcining the resulting gel, or by pyrolyzing an easily decomposable salt of the principal constituent element of the desired catalyst in air.

Solid acid catalysts falling under the category of the catalytic substance (2) can be prepared, for example, by adding sodium sulfide or potassium selenide to a water-soluble salt of the principal constituent element of the desired catalyst or by contacting the principal constituent element of the desired catalyst or a salt thereof with hydrogen sulfide gas or hydrogen selenide gas.

Metallic catalysts falling under the category of the catalytic substance (4) can be prepared, for example, by reducing a salt, hydroxide or oxide of the principal constituent element of the desired catalyst by means of a reducing agent such as hydrogen, formalin, formic acid, phosphorous acid, hydrazine or the like.

In the process of the present invention, the above-described catalytic substances (1), (2), (3) and (4) may be used alone or in admixture. Moreover, these catalytic substances and mixtures thereof may be used as such or in the form of supported catalysts. Although any carriers that are in common use for this purpose can be used, diatomaceous earth, pumice, titania, silica-alumina, alumina, magnesia, silica gel, activated carbon, activated clay, asbestos and the like are used in typical cases. Supported catalysts can be prepared by supporting the above-described catalytic substances on these carriers according to any conventional techniques. No particular limitation is placed on the amount of catalytic substance supported on the carrier. Usually, depending on the type of carrier used, any suitable amount (for example, from 1 to 50%) of catalytic substance may be supported thereon.

In addition, various types of activated carbon can be used in the process of the present invention. They include, for example, products made from coconut shell, wood, sawdust, lignin, coal, blood charcoal, bone char, coal, petroleum carbon and the like. They are commercially available in powdered form, in crushed form, or in shaped form (for example, in the shape of globules or cylinders). However, no particular limitation is placed on the form of activated carbon used.

Among the solid acid catalysts falling under the category of the catalytic substance (3), the sulfates and particularly cadmium sulfate are preferred for the purpose of obtaining the desired product in good yield. Among the solid acid catalysts falling under the category of the catalytic substance (2), platinum sulfide and palladium sulfide are particularly preferred. Among the metallic catalysts falling under the category of the catalytic substance (4), Ag is preferred.

Although the process of the present invention can be carried out in the vapor phase, the liquid phase or a mixed vapor-liquid phase, it is usually carried out in the vapor phase. Where the process of the present invention is carried out in the vapor phase, a fixed-bed, fluidized-bed or moving-bed reactor can be used to effect the reaction by heating the vapors of an aniline and an ethanolamine in the presence or absence of a catalyst. In this case, various inert gaseous substances may coexist as diluents for the vapors of the starting materials. The useful inert gaseous substances include, for example, nitrogen gas, carbon dioxide gas, water vapor, and the vapors of compounds that are inert to this reaction. Moreover, hydrogen gas or a hydrogen-containing gas may be used as a diluent.

The use of hydrogen gas or a hydrogen-containing gas is especially suitable for the purpose of maintaining the activity of the catalyst.

Similarly, owing to its ability to suppress the decomposition of the ethanolamine over the catalyst, the use of water vapor is suitable for the purpose of maintaining the activity of the catalyst and enhancing the yield of the desired product.

The amounts of aniline and ethanolamine fed to the reactor should be such that from 0.01 to 5 moles and preferably from 0.05 to 2 moles of the ethanolamine is provided for each mole of the aniline. If the amounts are outside this range, a reduction in yield will be caused and/or large amounts of by-products will be formed. These starting materials are fed, after being vaporized in advance or directly in liquid form, to the reactor at a liquid space velocity of from 0.01 to 5 liters/liter of the catalyst/hour.

The process of the present invention is carried out at a reaction temperature in the range of from 200° to 600° C. and preferably from 250° to 500° C. If the reaction temperature is lower than 200° C., the reaction can hardly proceed, while if it is higher than 600° C., undesirably large amounts of by-products will be formed.

The reaction pressure may be superatmospheric, atmospheric or subatmospheric.

Where the process of the present invention is carried out in the liquid phase or a mixed vapor-liquid phase, the reaction is effected by heating a mixture of an aniline and an ethanolamine in the presence of at least one member selected from the above-described catalysts. In this case, various inert gaseous substances and/or solvents may coexist as diluents for the starting materials. The useful inert gaseous substances include, for example, nitrogen gas, carbon dioxide gas, water vapor and the vapors of compounds that are inert to this reaction. The useful solvents include, for example, benzene, toluene, xylene, methanol, ethanol, isopropanol, dioxane, dimethylformamide, dimethyl sulfoxide, pyridine, N- methylpyrrolidone, trimethylamine, diethylamine, triethylamine, tripropylamine, tributylamine, diphenylamine, triphenylamine and other organic solvents.

In the case of liquid-phase reaction, the process of the present invention can be carried out in a fixed-bed, fluidized-bed or moving-bed reactor or in a rotary or continuous reactor for liquid-phase reactions. However, no particular limitation is placed on the type of reactor used.

The amounts of aniline and ethanolamine used as the starting materials for this reaction should be such that from 0.05 to 5 moles and preferably from 0.1 to 2 moles of the ethanolamine is provided for each mole of the aniline.

No particular limitation is placed on the amount of catalyst used for this reaction. However, the catalyst is generally used in an amount of from 0.01 to 20 g and preferably from 0.1 to 10 g of the active component thereof per mole of the aniline used as one of the starting materials.

The reaction temperature should be in the range of from 200° to 500° C. and preferably from 250° to 400° C. If the reaction temperature is lower than 200° C., the reaction can hardly proceed, while if it is higher than 500° C., undesirably large amounts of by-products will be formed.

The reaction pressure may be superatmospheric or atmospheric.

In various embodiments of the present invention, indole or a derivative thereof can readily be obtained in pure form by isolating it from the reaction product according to any conventional technique such as distillation.

The present invention is further illustrated by the following examples.

EXAMPLE 1

A 25-mm flow reactor made of Pyrex glass was packed with 50 ml of a palladium-carbon catalyst in cylindrical form (having a Pd content of 0.5%). The front end of this reactor was connected with a feed inlet pipe and a gas inlet pipe to form a feed vaporization zone, while the rear end thereof was connected with a receiver by way of an air-cooling zone. In the reaction zone, the internal temperature of the reactor was kept at 325° C. After the catalyst was reduced by passing hydrogen gas through the reactor for about 1 hour, a mixture consisting of 9.3 g (0.1 mole) of aniline and 6.1 g (0.1 mole) of monoethanolamine was introduced thereinto through the feed inlet pipe at a liquid space velocity of 0.1 liter/liter of the catalyst/hour. At the same time, nitrogen gas at atmospheric pressure was passed therethrough in an amount of 10 moles per mole of the aniline used as one of the starting materials. The reaction product withdrawn from the reactor, condensed and collected in the receiver was analyzed by gas chromatography. This revealed that 7.1 g of indole was obtained in a 60.5% yield based on the aniline and accompanied with very small amounts of by-products.

EXAMPLE 2

Reaction was carried out in the same manner as described in Example 1 except that various ethanolamines were used in place of the monoethanolamine. The type and amount of ethanolamines used and the results thus obtained are summarized in Table 1.

TABLE 1

| Run No. | Ethanolamine Type | Amount g | Amount mole | Amount (g) | Yield of Indole Percentage Based on Aniline |
|---|---|---|---|---|---|
| 1 | Diethanolamine | 9.3 | 0.1 | 7.5 | 63.4 |
| 2 | Triethanolamine | 7.5 | 0.05 | 4.2 | 42.4 |
| 3 | Diethanolamine | 5.3 | 0.05 | 6.5 | 55.6 |
|   | Triethanolamine | 4.5 | 0.03 |   |   |
| 4 | Monoethanolamine | 6.1 | 0.1 |   |   |
|   | Diethanolamine | 5.3 | 0.05 | 8.3 | 70.6 |
|   | Triethanolamine | 4.5 | 0.03 |   |   |

EXAMPLE 3

Reaction was carried out in the same manner as described in Example 1 except that 6.1 g (0.1 mole) of monoethanolamine or 9.3 g (0.1 mole) of diethanolamine was used in combination with a variety of catalysts. The types of ethanolamines and catalysts used and the results thus obtained are summarized in Table 2.

TABLE 2

| Run No. | Ethanolamine* | Catalyst | Amount (g) | Yield of Indole Percentage Based on Aniline |
|---|---|---|---|---|
| 5 | M | Pd—CaCO$_3$ (with a Pd content of 5%) | 5.7 | 49.1 |
| 6 | D | Pd—CaCO$_3$ (with a Pd content of 5%) | 6.7 | 57.5 |
| 7 | M | Pt—C (with a Pt content of 0.5%) | 5.8 | 49.4 |
| 8 | D | Pt—Silica gel (with a Pt content of 5%) | 6.1 | 52.3 |
| 9 | D | Rh—alumina (with an Rh content of 5%) | 3.0 | 25.4 |
| 10 | M | Os—C (with an Os content of 5%) | 3.8 | 32.8 |
| 11 | D | Os—C (with an Os content of 5%) | 4.6 | 39.6 |
| 12 | D | Ir—asbestos (with an Ir content of 5%) | 2.8 | 23.7 |
| 13 | M | Ru—alumina (with an Ru content of 5%) | 2.3 | 19.6 |
| 14 | D | Ni—diatomaceous earth (with an Ni content of 50%) | 3.4 | 29.3 |
| 15 | D | Cu—diatomaceous earth (with a Co content of 50%) | 3.5 | 29.6 |
| 16 | M | Fe—diatomaceous earth (with an Fe content of 50%) | 2.7 | 23.1 |
| 17 | M | Cu—C (with a Cu content of 5%) | 5.6 | 48.2 |
| 18 | D | Cu—C (with a Cu content of 5%) | 5.2 | 44.5 |
| 19 | M | Cu—SiO$_2$ (with a Cu content of 5%) | 5.2 | 44.3 |
| 20 | D | Cu—SiO$_2$ (with a Cu content of 5%) | 5.1 | 43.6 |
| 21 | M | Ag—C (with an Ag content of 1%) | 4.4 | 37.7 |
| 22 | D | Au—C (with an Au content of 0.5%) | 4.0 | 34.0 |
| 23 | M | ZnCl$_2$ (with a ZnCl$_2$ content of 20%) | 5.5 | 47.0 |
| 24 | D | ZnCl$_2$ (with a ZnCl$_2$ content of 20%) | 6.1 | 52.5 |
| 25 | M | ZnSO$_4$—C (with a ZnSO$_4$ content of 5%) | 5.7 | 48.7 |
| 26 | M | Zinc phosphate | 5.5 | 46.8 |
| 27 | D | Zinc phosphate | 6.0 | 51.7 |
| 28 | M | CdCl$_2$—CaCl$_2$ (with a CdCl$_2$ content of 50%) | 6.1 | 51.9 |
| 29 | M | CdSO$_4$ | 6.8 | 58.0 |

TABLE 2-continued

| Run No. | Ethanol-amine* | Catalyst | Yield of Indole Amount (g) | Percentage Based on Aniline |
|---|---|---|---|---|
| 30 | D | CdSO₄ | 7.1 | 60.3 |
| 31 | D | CdSO₄—C (with a CdSO₄ content of 5%) | 6.6 | 56.6 |
| 32 | D | Cadmium phosphate | 6.5 | 55.2 |
| 33 | D | Magnesium pyrophosphate | 7.2 | 61.4 |
| 34 | D | MgO—C (with an MgO content of 5%) | 7.7 | 65.5 |

*M stands for ethanolamine and D for diethanolamine.

EXAMPLE 4

Reaction was carried out in the same manner as described in Example 1 except that granular activated carbon was used in place of the Pd-C catalyst, 6.1 g (0.1 mole) of monoethanolamine or 9.3 g (0.1 mole) of diethanolamine was used as the ethanolamine, and the reaction temperature was raised to 400° C. When monoethanolamine was used, 2.7 g of indole was obtained in a 23.5% yield based on the aniline. Similarly, when diethanolamine was used, 2.9 g of indole was obtained in a 24.5% yield based on the aniline.

EXAMPLE 5

Reaction was carried out in the same manner as described in Example 1 except that a Pd-C catalyst (having a Pd content of 5%) was used in place of the Pd-C catalyst (having a Pd content of 0.5%), hydrogen gas was used in place of the nitrogen gas, and 6.1 g (0.1 mole) of monoethanolamine or 9.3 g (0.1 mole) of diethanolamine was used as the ethanolamine. When monoethanolamine was used, 7.7 g of indole was obtained in a 66.0% yield based on the aniline. Similarly, when 7.8 g of indole was obtained in a 66.7% yield based on the aniline.

EXAMPLE 6

Reaction was carried out in the same manner as described in Example 1 except that various combinations of anilines and ethanolamines were used. The types of aniline and ethanolamines used and the results thus obtained are summarized in Table 3.

TABLE 3

| Run No. | Aniline* | Ethanol-amine** | Type of Product | Yield of Product Amount (g) | Percentage Based on Aniline |
|---|---|---|---|---|---|
| 35 | T | M | 5-Methylindole | 1.6 | 12.4 |
| 36 | T | D | 5-Methylindole | 1.8 | 13.9 |
| 37 | A | M | 5-Methoxyindole | 1.7 | 11.9 |
| 38 | A | D | 5-Methoxyindole | 2.0 | 13.3 |

*T stands for 10.7 g (0.1 mole) of p-toluidine and A for 12.3 g (0.1 mole) of p-anisidine.
**M stands for 6.1 g (0.1 mole) of monoethanolamine and D for 9.3 g (0.1 mole) of diethanolamine.

EXAMPLE 7

Into a 200-ml autoclave made of a titanium alloy and fitted with a stirrer were charged 93.1 g (1 mole) of aniline, 10.6 g (0.1 mole) of diethanolamine, and 1 g of a palladium-carbon catalyst in powder form (having a Pd content of 0.5%). After the autoclave was purged with nitrogen gas and filled therewith at a pressure of 5 kg/cm², reaction was carried out at 300° C. for 30 minutes with stirring. After completion of the reaction, the catalyst was separated from the reaction mixture by filtration and the resulting reaction product was analyzed by gas chromatography. Furthermore, the reaction product was subjected to distillation and the formation of indole was confirmed by IR and NMR spectroscopy. This revealed that 4.4 g of indole was formed in a 38.0% yield based on the diethanolamine and accompanied with a small amount of indoline formed as a by-product.

EXAMPLE 8

Cadmium sulfide in powder form was compressed and then crushed to particles. A 10-mm flow reactor made of Pyrex glass was packed with 5 ml of the particles. The front end of this reactor was connected with a feed inlet pipe and a gas inlet pipe to form a feed vaporization zone, while the rear end thereof was connected with a receiver by way of an air-cooling zone. In the reaction zone, the internal temperature of the reactor was kept at 325° C. Then, a mixture consisting of 1 mole of aniline and 0.2 mole of monoethanolamine was introduced thereinto through the feed inlet pipe at a liquid space velocity of 0.1 liter/liter of the catalyst/hour. At the same time, nitrogen gas at atmospheric pressure was passed therethrough in an amount of 10 moles per mole of the aniline used as one of the starting materials. After the reaction was carried out for 3 hours, the resulting reaction product was analyzed by gas chromatography. This revealed that indole was obtained in a 55% yield based on the monoethanolamine and accompanied with very small amounts of by-products.

EXAMPLE 9

Reaction was carried out in the same manner as described in Example 8 except that various catalysts were used in place of the cadmium sulfide. The results thus obtained are summarized in Table 4.

TABLE 4

| Run No. | Type of Catalyst | Yield of Indole (%) |
|---|---|---|
| 39 | ZnS | 30 |
| 40 | ZnSe | 15 |
| 41 | CdSe | 52 |
| 42 | SrSO₄ | 12 |
| 43 | NiSO₄ 6H₂O | 20 |
| 44 | MgSO₄ 7H₂O | 26 |
| 45 | BeSO₄ 7H₂O | 38 |
| 46 | CoSO₄ 7H₂O | 40 |
| 47 | MgCl₂ 6H₂O | 42 |

EXAMPLE 10

The procedure of Example 8 was repeated except that 5 ml of glass beads having a diameter of 2 mm was used in place of the catalyst of Example 8. As a result, indole was obtained in a 1% yield. Then, the same procedure was repeated once more at a reaction temperature of 500° C. to obtain indole in a 6% yield.

EXAMPLE 11

Using the catalyst of Example 8, reaction was carried out for 27 hours in the same manner as described in Example 8. The reaction mixture collected between the start of the reaction and 3 hours after that (hereinafter referred to as reaction mixture A) and the reaction mixture collected between 24 hours and 27 hours after the start of the reaction (hereinafter referred to as reaction mixture B) were analyzed. This revealed that the yield of indole was 56% for reaction mixture A and 19% for reaction mixture B.

What is claimed is:

1. A process for the preparation of an indole which comprises the step of contacting an aniline selected from the group consisting of aniline, o-toluidine, m-toluidine, p-toluidine, o-haloaniline, m-haloaniline, p-haloaniline, o-aminophenol, m-aminophenol, p-aminophenol, o-anisidine, m-anisidine and p-anisidine with an ethanolamine selected from the group consisting of monoethanolamine, diethanolamine and triethanolamine in the presence of a solid acid catalyst, in the vapor phase at a temperature of from 200° to 600° C., or in the liquid phase or a mixed vapor-liquid phase at a temperature of from 200° to 500° C.

2. A process as claimed in claim 1 wherein said indole is indole.

3. A process as claimed in claim 1 wherein the reaction is carried out in the vapor phase at a temperature of from 200° to 600° C. and 0.01 to 5 moles of said ethanolamine is provided for each mole of said aniline.

4. A process as claimed in claim 1 wherein the reaction is carried out in the liquid phase or a mixed vapor-liquid phase at a temperature of from 200° to 500° C. and 0.05 to 5 moles of said ethanolamine is provided for each mole of said aniline.

5. A process as claimed in claim 1 wherein the reaction is carried out in an atmosphere of hydrogen gas or a mixture of hydrogen and an inert gas.

6. A process as claimed in claim 1 wherein the reaction is carried out in the presence of water or water vapor.

7. A process as claimed in claim 1 wherein the solid acid catalyst is a catalyst containing an oxide or hydroxide of at least one element selected from the group consisting of Si, Al, B, Sb, Bi, Sn, Pb, Ga, Ti, Zr, Be, Mg, Y, Cu, Ag, Zn, Cd and the lanthanides.

8. A process as claimed in claim 1 wherein the solid acid catalyst is a catalyst containing a sulfide or selenide of at least one element selected from the group consisting of Pd, Pt, Cr, Fe, Ni, Co, Zn, Mo, Cd and W.

9. A process as claimed in claim 1 wherein the solid acid catalyst is a catalyst containing an inorganic acid salt of at least one element selected from the group consisting of Fe, Tl, Ca, Mn, Bi, Sr, Y, Al, Zn, Cd, Ni, Mg, In, Be, Co, Ga and the lanthanides.

10. A process as claimed in claim 9 wherein the inorganic acid salt is a sulfate.

11. A process as claimed in claim 8 or 10 wherein one of the constituent elements of the catalyst is Cd.

* * * * *